(12) United States Patent
Turner et al.

(10) Patent No.: US 8,162,000 B2
(45) Date of Patent: Apr. 24, 2012

(54) ADJUSTABLE PNEUMATIC SYSTEM FOR A SURGICAL MACHINE

(75) Inventors: Denis Turner, Vista, CA (US); Argelio Olivera, Mission Viejo, CA (US); John Huculak, Mission Viejo, CA (US); Mark Hopkins, Mission Viejo, CA (US)

(73) Assignee: Novartis AG, Basel (CH)

( * ) Notice: Subject to any disclaimer, the term of this patent is extended or adjusted under 35 U.S.C. 154(b) by 308 days.

(21) Appl. No.: 11/610,275

(22) Filed: Dec. 13, 2006

(65) Prior Publication Data
US 2008/0142093 A1    Jun. 19, 2008

(51) Int. Cl.
*F16K 31/12* (2006.01)
(52) U.S. Cl. .............. 137/487.5; 137/102; 137/613
(58) Field of Classification Search .......... 137/102, 137/487.5, 512, 596, 613
See application file for complete search history.

(56) References Cited

U.S. PATENT DOCUMENTS

| | | |
|---|---|---|
| 812,162 A | 2/1906 | Bemis |
| 2,016,746 A | 10/1935 | Ireland |
| 2,707,389 A | 5/1955 | Fortier |
| 3,084,674 A | 4/1963 | Watson |
| 3,646,727 A | 3/1972 | Wachsmuth |
| 3,703,139 A | 11/1972 | Furlong |
| 3,726,307 A | 4/1973 | Carman et al. |
| 3,867,934 A | 2/1975 | Ollivier |
| 4,075,928 A | 2/1978 | Bitonti |
| 4,077,567 A | 3/1978 | Ginn et al. |
| 4,086,804 A | 5/1978 | Ruby |
| 4,253,480 A * | 3/1981 | Kessel et al. ............ 137/102 |
| 4,323,064 A | 4/1982 | Hoenig et al. |
| 4,331,130 A | 5/1982 | Lewicky |
| 4,344,144 A | 8/1982 | Damico et al. |
| 4,476,532 A | 10/1984 | Akiyama et al. |
| 4,590,935 A | 5/1986 | Ranalli |
| 4,622,503 A | 11/1986 | Sundblom et al. |
| 4,650,460 A | 3/1987 | Roizenblatt |
| 4,650,462 A | 3/1987 | Desatnick et al. |
| 4,679,583 A | 7/1987 | Lucas et al. |

(Continued)

FOREIGN PATENT DOCUMENTS

DE    39 25 405 A1    2/1991

(Continued)

OTHER PUBLICATIONS

Non-Final Office Action, U.S. Appl. No. 11/554,387, Sep. 17, 2009, 23 pages.

(Continued)

*Primary Examiner* — Craig Schneider
*Assistant Examiner* — Craig Price
(74) *Attorney, Agent, or Firm* — Darien Reddick

(57) ABSTRACT

A pneumatic system for a surgical machine includes a reservoir, first and second proportional valves, and a controller. The reservoir holds pressurized gas. The first proportional valve is located on an input side of the reservoir and allows a variable amount of pressurized gas to enter the reservoir. The second proportional valve is located on an output side of the reservoir and allows a second variable amount of pressurized gas to exit the reservoir. The controller controls the operation of the first and second proportional valves. The controller adjusts the first and second proportional valves so that a constant gas pressure range is maintained at an output of the reservoir over a first range of input gas pressures and a second range of gas usage.

15 Claims, 4 Drawing Sheets

U.S. PATENT DOCUMENTS

| | | | |
|---|---|---|---|
| 4,706,687 A | | 11/1987 | Rogers et al. |
| 4,757,814 A | | 7/1988 | Wang et al. |
| 4,770,654 A | | 9/1988 | Rogers et al. |
| 4,790,816 A | | 12/1988 | Sundblom et al. |
| 4,810,242 A | | 3/1989 | Sundblom et al. |
| 4,840,111 A | | 6/1989 | Garnjost |
| 4,887,636 A | | 12/1989 | Rothen |
| 4,933,843 A | | 6/1990 | Scheller et al. |
| 5,094,260 A | | 3/1992 | Stuart et al. |
| 5,138,838 A | | 8/1992 | Crosser |
| 5,176,628 A | | 1/1993 | Charles et al. |
| 5,239,861 A | | 8/1993 | Fujita et al. |
| 5,279,322 A | | 1/1994 | Nakamura et al. |
| 5,314,295 A | | 5/1994 | Lukkari et al. |
| 5,318,072 A | | 6/1994 | Goedecke |
| 5,417,246 A | | 5/1995 | Perkins et al. |
| 5,549,139 A | * | 8/1996 | Perkins et al. ................ 137/884 |
| 5,571,248 A | * | 11/1996 | Seetharaman et al. ... 137/625.65 |
| 5,580,347 A | | 12/1996 | Reimels |
| 5,587,536 A | | 12/1996 | Rasmussen |
| 5,674,194 A | | 10/1997 | Jung et al. |
| 5,829,335 A | | 11/1998 | Ewald et al. |
| 5,846,257 A | | 12/1998 | Hood |
| 5,857,485 A | * | 1/1999 | Perkins et al. ............ 137/487.5 |
| 5,979,494 A | | 11/1999 | Perkins et al. |
| 6,065,494 A | | 5/2000 | Thomsen et al. |
| 6,155,233 A | * | 12/2000 | Wade et al. .................... 123/458 |
| 6,155,289 A | | 12/2000 | Carlsen et al. |
| 6,450,966 B1 | | 9/2002 | Hanna |
| 6,474,289 B1 | | 11/2002 | Lilly et al. |
| 6,575,990 B1 | | 6/2003 | Wang et al. |
| 6,655,404 B2 | | 12/2003 | Hilaire |
| 6,779,541 B2 | * | 8/2004 | Inayama et al. ............. 137/102 |
| 7,089,733 B1 | | 8/2006 | Jackson et al. |
| 7,244,240 B2 | | 7/2007 | Nazarifar et al. |
| 7,335,217 B2 | | 2/2008 | Wang et al. |
| 7,470,277 B2 | | 12/2008 | Finlay et al. |
| 7,814,936 B2 | * | 10/2010 | Catron .......................... 137/828 |
| 2002/0069916 A1 | | 6/2002 | Ferguson et al. |
| 2002/0117214 A1 | * | 8/2002 | Tucker et al. ............. 137/487.5 |
| 2002/0174905 A1 | | 11/2002 | Latino et al. |
| 2003/0042182 A1 | | 3/2003 | Moscaritolo |
| 2006/0271082 A1 | | 11/2006 | Kirchhevel et al. |
| 2007/0270735 A1 | | 11/2007 | Williams et al. |
| 2007/0270746 A1 | | 11/2007 | King |
| 2007/0282262 A1 | | 12/2007 | Williams et al. |
| 2008/0082077 A1 | | 4/2008 | Williams |
| 2008/0142093 A1 | | 6/2008 | Turner et al. |
| 2008/0146988 A1 | | 6/2008 | Olivera et al. |
| 2008/0149197 A1 | | 6/2008 | Turner et al. |
| 2008/0168985 A1 | | 7/2008 | Turner et al. |
| 2009/0124962 A1 | | 5/2009 | Hopkins et al. |
| 2009/0203480 A1 | | 8/2009 | Petzold et al. |
| 2009/0259242 A1 | | 10/2009 | Gerg et al. |
| 2009/0270793 A1 | | 10/2009 | Domash et al. |

FOREIGN PATENT DOCUMENTS

| | | |
|---|---|---|
| DE | 42 32 586 A1 | 3/1994 |
| DE | 198 21 420 C1 | 10/1999 |
| DE | 10247869 A1 | 5/2004 |
| DE | 10341477 | 3/2005 |
| DE | 20 2005 009670 U1 | 9/2005 |
| DE | 10247869 B4 | 2/2007 |
| EP | 0469641 B1 | 6/1989 |
| EP | 0626628 A1 | 11/1994 |
| EP | 0626628 B1 | 12/1997 |
| EP | 0673475 B1 | 6/1998 |
| EP | 874163 A2 | 10/1998 |
| EP | 0884667 A1 | 12/1998 |
| EP | 1 172 586 A1 | 1/2002 |
| EP | 1660244 B1 | 12/2006 |
| EP | 2032878 | 12/2009 |
| GB | 792397 | 3/1958 |
| GB | 1 213 723 | 11/1970 |
| GB | 2016746 | 9/1979 |
| GB | 2 389 423 A | 12/2003 |
| JP | 07259801 A | 10/1995 |
| JP | 09225698 A | 9/1997 |
| WO | WO 95/31141 A1 | 11/1995 |
| WO | WO 00/78371 A1 | 12/2000 |
| WO | WO 01/64120 A1 | 9/2001 |
| WO | WO 2008/000599 A1 | 1/2008 |
| WO | WO 2008/054944 A1 | 5/2008 |
| WO | WO 2008/105950 A2 | 9/2008 |
| WO | WO 2008/105950 A3 | 9/2008 |
| WO | 2008140537 A1 | 11/2008 |
| WO | 2008/0147429 | 12/2008 |
| WO | 2008147429 A2 | 12/2008 |
| WO | WO 2008147429 A3 | 12/2008 |

OTHER PUBLICATIONS

International Searching Authority, PCT International Preliminary Report on Patentability, PCT/US2007/079915, May 15, 2009, 6 pages.

International Searching Authority, PCT International Preliminary Report on Patentability, PCT/US2007/080265, Sep. 1, 2009, 8 pages.

International Searching Authority, PCT International Preliminary Report on Patentability, PCT/US2007/080540, Jun. 23, 2009, 5 pages.

Final Office Action, U.S. Appl. No. 11/610,275, Sep. 14, 2009, 18 pages.

International Searching Authority, PCT International Preliminary Report on Patentability, PCT/US2007/080239, Jun. 16, 2009, 8 pages.

Kabei, Shimemura, et al., A portable pneumatic driving unit for a left ventricular assist device, Int. J. Artif. Organs, 1988, 186-90, 11(3).

Nachlas, Marvin, et al., A simple portable pneumatic pump for external cardiac massage, The American Journal of Cardiology, 1962, 107-109, 10(1).

J.L. Waldeck; "The Development of a Portable Pressure Source for the Static and Dynamic Calibration of Pressure Transducers"; Journal of Wind Engineering and Industrial Aerodynamics, 1987, 26(2), 213-230.

Ellis, George, et al., Microcomputer-Controlled Precision Pressure Generator, IEEE Transactions on Instrumentation and Measurement, 1977, 214-217, 26(3).

Whalen, R.L., et al., An electromagnetic pneumatic blood pump driver, American Society of Artificial Internal Organs, 1988, 721-725, 34(3).

Turkentine, R.B., et al., Pressure-operated shutter for thin-film monitor, Journal of Physics E: Scientific Instruments, 1979, 12(1).

Rogers, Richard C., An inexpensive picoliter-volume pressure ejection system, Brain Research Bulletin, 1985, 669-671, 15(6).

Johnson, Kenneth S., et al., A submersible flow analysis System, Analytical Chimica Acta, 1986, 245-257, 179.

Tabassum, Alim Abid, Solar refrigeration: evaluation of technical options and design of a solar-generator-adsorber for a novel adsorption refrigerator, Cranfield Univ., 1989.

Buchanan, P.R., et al., Recovery of ventilation distributions by gas wash-out of a mechanical pump, Clinical Physics and Physiological Measurement, 1986, 7(3).

International Search Report for PCT/US2007/080239, Publication No. WO2008/140537, 3 pages.

International Search Report for PCT/US2007/079915, Publication No. WO2008/054944, 2 pages.

International Search Report for PCT/US2007/080265, Publication No. WO2008/105950, 3 pages.

International Search Report for PCT/US2007/080540, Publication No. WO2008/147429, 4 pages.

Office Action, U.S. Appl. No. 11/610,275, Nov. 25, 2008, 10 pages.

Office Action, U.S. Appl. No. 11/610,275, Apr. 13, 2009, 16 pages.

* cited by examiner

ADJUSTABLE PNEUMATIC SYSTEM FOR A SURGICAL MACHINE

FIELD OF THE INVENTION

The present invention relates to a pneumatic module for a surgical machine and more particularly to a pneumatic module with a dynamically adjustable pressure set point.

BACKGROUND OF THE INVENTION

Vitreo-retinal procedures include a variety of surgical procedures performed to restore, preserve, and enhance vision. Vitreo-retinal procedures are appropriate to treat many serious conditions of the back of the eye. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

The vitreous is a normally clear, gel-like substance that fills the center of the eye. It makes up approximately two-thirds of the eye's volume, giving it form and shape before birth. Certain problems affecting the back of the eye may require a vitrectomy, or surgical removal of the vitreous.

A vitrectomy may be performed to clear blood and debris from the eye, to remove scar tissue, or to alleviate traction on the retina. Blood, inflammatory cells, debris, and scar tissue obscure light as it passes through the eye to the retina, resulting in blurred vision. The vitreous is also removed if it is pulling or tugging the retina from its normal position. Some of the most common eye conditions that require a vitrectomy include complications from diabetic retinopathy such as retinal detachment or bleeding, macular hole, retinal detachment, pre-retinal membrane fibrosis, bleeding inside the eye (vitreous hemorrhage), injury or infection, and certain problems related to previous eye surgery.

A retinal surgeon performs a vitrectomy with a microscope and special lenses designed to provide a clear image of the back of the eye. Several tiny incisions just a few millimeters in length are made on the sclera. The retinal surgeon inserts microsurgical instruments through the incisions such as a fiber optic light source to illuminate inside the eye, an infusion line to maintain the eye's shape during surgery, and instruments to cut and remove the vitreous.

In a vitrectomy, the surgeon creates three tiny incisions in the eye for three separate instruments. These incisions are placed in the pars plana of the eye, which is located just behind the iris but in front of the retina. The instruments which pass through these incisions include a light pipe, an infusion port, and the vitrectomy cutting device or vitrector. The light pipe is the equivalent of a microscopic high-intensity flashlight for use within the eye. The infusion port is required to replace fluid in the eye and maintain proper pressure within the eye. The vitrector, or cutting device, works like a tiny guillotine, with an oscillating microscopic cutter to remove the vitreous gel in a controlled fashion. This prevents significant traction on the retina during the removal of the vitreous humor.

The surgical machine used to perform a vitrectomy and other surgeries on the posterior of the eye is very complex. Typically, such an ophthalmic surgical machine includes a main console to which the numerous different tools are attached. The main console provides power to and controls the operation of the attached tools.

The attached tools typically include probes, scissors, forceps, illuminators, vitrectors, and infusion lines. Each of these tools is typically attached to the main surgical console. A computer in the main surgical console monitors and controls the operation of these tools. These tools also get their power from the main surgical console. Some of these tools are electrically powered while others are pneumatically powered.

In order to provide pneumatic power to the various tools, the main surgical console has a pneumatic module. This pneumatic module conditions and supplies compressed air or gas to power the tools. Typically, the pneumatic module is connected to a cylinder that contains compressed gas. The pneumatic module must provide the proper gas pressure to operate the attached tools properly. Providing different pressures to a tool can alter the way in which it operates over that range of pressures. For example, it is desirable to provide a low gas pressure when a vitrector is operated at a relatively low cut rate, and it is necessary to provide a high gas pressure when a vitrector is being operated at a high cut rate.

It would be desirable to have a pneumatic module that provides a dynamic range of pressures so that the attached tools can be used over their full operating ranges.

SUMMARY OF THE INVENTION

In one embodiment consistent with the principles of the present invention, the present invention is a pneumatic system for a surgical machine. The system includes a reservoir, first and second proportional valves, and a controller. The reservoir holds pressurized gas. The first proportional valve is located on an input side of the reservoir and allows a variable amount of pressurized gas to enter the reservoir. The second proportional valve is located on an output side of the reservoir and allows a second variable amount of pressurized gas to exit the reservoir. The controller controls the operation of the first and second proportional valves. The controller adjusts the first and second proportional valves so that a constant gas pressure range is maintained at an output of the reservoir over a first range of input gas pressures and a second range of gas usage.

In another embodiment consistent with the principles of the present invention, the present invention is a pneumatic system for a surgical machine. The system includes a reservoir, first and second proportional valves, a controller, first and second interfaces, and input and output pressure transducers. The reservoir holds pressurized gas. The first proportional valve is located on an input side of the reservoir and allows a variable amount of pressurized gas to enter the reservoir. The second proportional valve is located on an output side of a reservoir and allows a variable amount of pressurized gas to exit the reservoir. The controller is adapted to control the operation of the first and second proportional valves, thereby adjusting an amount of pressurized gas entering and exiting the reservoir. The first interface electrically couples the first proportional valve to the controller. The second interface electrically couples the second proportional valve to the controller. The output pressure transducer is located on the output side of the reservoir, measures a pressure of the pressurized gas exiting the reservoir, and is electrically coupled to the controller. The input pressure transducer is located on an input side of the reservoir, measures a pressure of the pressurized gas near the first proportional valve, and is electrically coupled to the controller. The controller receives a first signal from the input pressure transducer corresponding to the pressure of the pressurized gas near the first proportional valve and a second signal from the output pressure transducer corresponding to the pressure of the pressurized gas exiting the reservoir. The controller uses the first and second signals to adjust the first and second proportional valves so that a constant gas pressure range is maintained in the reservoir over a first range of input gas pressures and a second range of gas usage.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
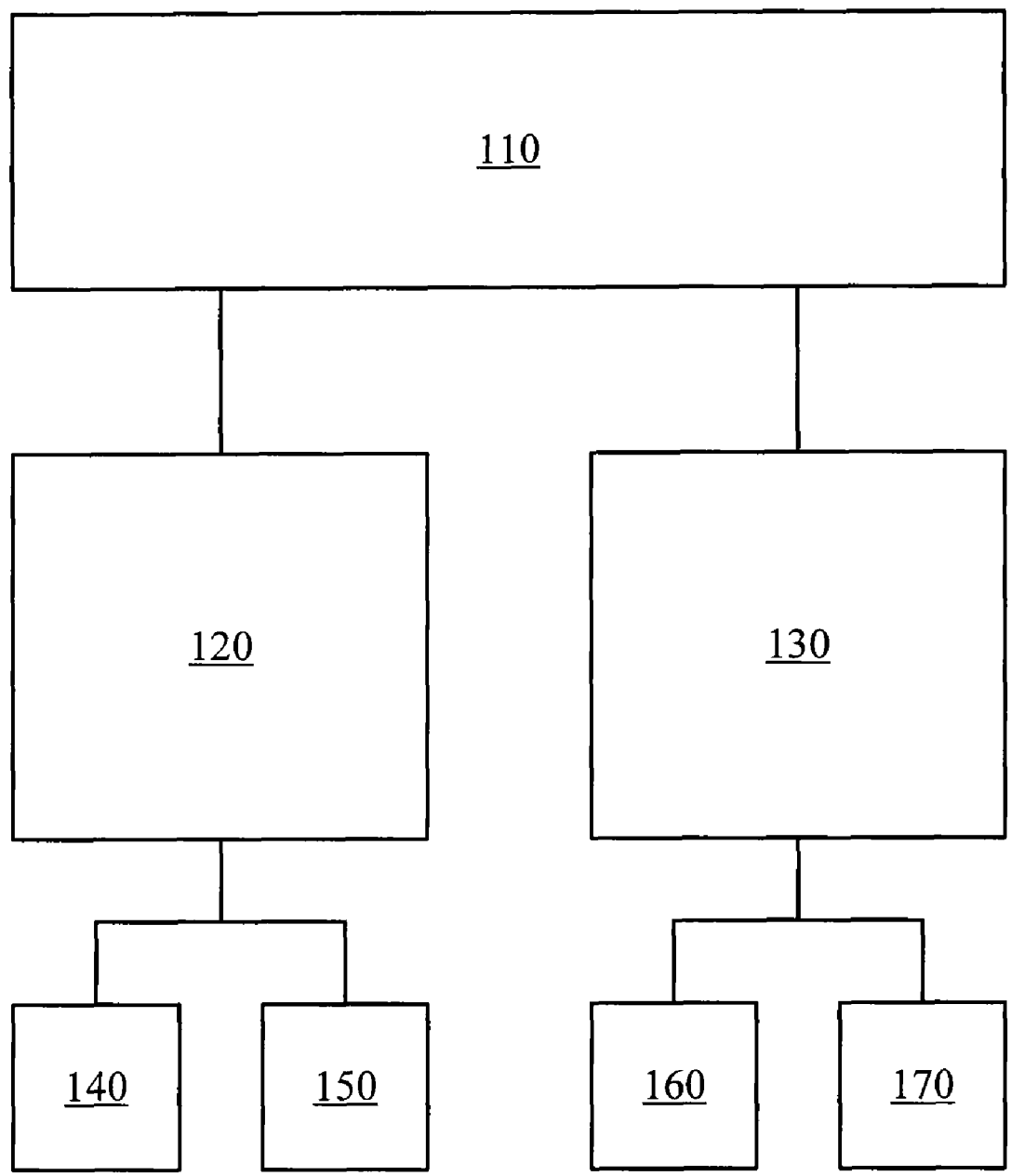
FIG. 1 is a block diagram of a pneumatically-powered ophthalmic surgery machine according to an embodiment of the present invention.

FIG. 1 is a block diagram of a pneumatically powered ophthalmic surgical machine according to an embodiment of the present invention. In FIG. 1, the machine includes gas pressure monitor system 110, proportional controllers 120 and 130, and tools 140, 150, 160, and 170. The tools 140, 150, 160, and 170 can be, for example, scissors, vitrectors, forceps, and injection or extraction modules. Other tools may also be employed with the machine of FIG. 1.

As shown in FIG. 1, gas pressure monitor system 110 is fluidly coupled via a manifold to proportional controllers 120 and 130. A single manifold may connect gas pressure monitor system 110 to proportional controllers 120 and 130, or two separate manifolds may connect gas pressure monitor system 110 to proportional controllers 120 and 130, respectively.

In operation, the pneumatically powered ophthalmic surgery machine of FIG. 1 operates to assist a surgeon in performing various ophthalmic surgical procedures, such as a vitrectomy. A compressed gas, such as nitrogen, provides the power for tools 140, 150, 160, and 170. The compressed gas passes through gas pressure monitor system 110, through one or more manifolds to proportional controllers 120 and 130, and through additional manifolds and/or tubing to tools 140, 150, 160, and 170.

Gas pressure monitor system 110 functions to monitor the pressure of compressed gas from a gas source as it enters the machine. Proportional controllers 120 and 130 serve to distribute the compressed gas received from gas pressure monitor system 110. Proportional controllers 120 and 130 control the pneumatic power delivered to tools 140, 150, 160, and 170. Various valves, manifolds, and tubing are used to direct compressed gas from gas pressure monitor system 110, through proportional controllers 120 and 130, and to tools 140, 150, 160, and 170. This compressed gas actuates cylinders, for example, in tools 140, 150, 160, and 170.

Figure 2:
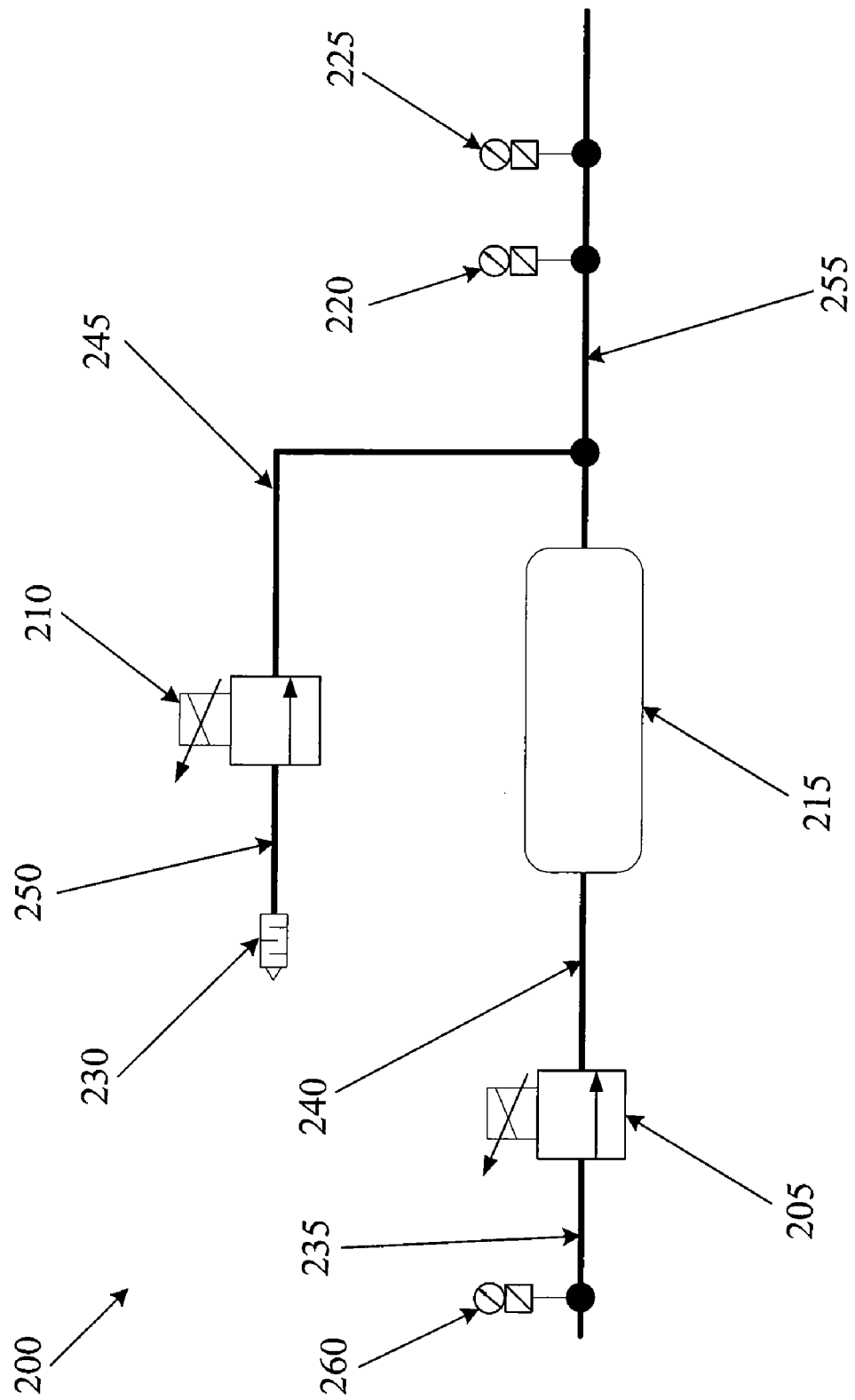
FIG. 2 is a schematic of a pneumatic system capable of providing a dynamic range of pressures according to an embodiment of the present invention.

FIG. 2 is a schematic of a pneumatic system capable of providing a dynamic range of pressures according to an embodiment of the present invention. In FIG. 2, the pneumatic system 200 includes input proportional valve 205, output proportional valve 210, reservoir 215, output pressure transducers 220 and 225, input pressure transducer 260, muffler 230, and manifolds 235, 240, 245, 250, and 255.

Manifold 235 connects input pressure transducer 260 to input proportional valve 205. Manifold 240 connects input proportional valve 205 to reservoir 215. Manifold 245 connects output proportional valve 210 to reservoir 215. Manifold 250 connects output proportional valve 210 to a venting port to which muffler 230 is attached. Manifold 255 connects reservoir 215 to output pressure transducers 220 and 225.

In the embodiment of FIG. 2, proportional valves 205 and 210 are standard adjustable valves. As is commonly known, a proportional valve has a solenoid that operates to move the valve to any number of positions. Proportional valves 205 and 210 can be opened to any degree within the operating parameters of the valve. Typically, the percentage that each proportional valve 205, 210 is capable of opening is any percentage in the range from 0% (fully closed) to 100% (fully open). For example, proportional valves 205 and 210 can be opened 10%, 20%, 30%, etc. to allow a precise quantity of gas to flow through them during a time period. Proportional valves 205 and 210 are independently controlled by a controller (not shown). In this manner, proportional valve 205 can be operated at one position while proportional valve 210 can be operated at another.

Input proportional valve 205 controls the flow of pressurized gas from manifold 235 to reservoir 215. In this manner, proportional valve 205 controls the amount of gas that enters reservoir 215 over a given time period. Output proportional valve 210 controls the amount of pressurized gas exhausted to the atmosphere from reservoir 215. In this manner, proportional valve 205 controls the amount of gas that exits reservoir 215 through manifold 250 and a venting port to which muffler 230 is attached.

Reservoir 215 is a chamber that is capable of holding pressurized gas. Typically, reservoir 215 is machined out of one or more pieces of aluminum. As such, reservoir 215 holds a set volume of gas at a pressure. When used, reservoir 215 is air tight. Reservoir 215 may also have couplings or fittings to connect to manifolds. In another embodiment consistent with the principles of the present invention, reservoir 215 and various manifolds may be machined out of a single piece of aluminum.

Pressure transducers 220, 225 and 260 operate to read an atmospheric pressure of the gas contained in manifolds 255, 245, and 235, respectfully. In other words, pressure transducers 220 and 225 read the pressure of the compressed gas that is adjacent to it in manifold 245 and 255. Two pressure transducers 220 and 225 are provided for redundancy. In this case, the pressure measured by the process can be more robust and less susceptible to transducer failure. Likewise, pressure transducer 260 reads the pressure of the compressed gas that is adjacent to it in manifold 235. In the embodiment of FIG. 2, pressure transducers 220, 225 and 260 are common pressure transducers. Pressure transducers 220, 225 and 260 are capable of reading pressure of a compressed gas and sending an electrical signal containing information about the pressure of the compressed gas to a controller (not shown).

Manifolds 235, 240, 245, 250, and 255 are all configured to carry compressed gas. In the embodiment of FIG. 2, these manifolds are machined out of a metal, such as aluminum. These manifolds are air tight, contain various fittings and couplings, and are designed to withstand relatively high gas pressures. These manifolds may be manufactured as individual pieces, or they may be manufactured as a single piece. For example, manifolds 235, 240, 245, 250, and 255 may be machined from a single piece of aluminum. In another embodiment consistent with the principles of the present invention, manifolds 235 and 240 may be machined from a single piece of aluminum, and manifolds 245, 250, and 255 may be machined from another piece of aluminum.

Muffler 230 is a common muffler designed to suppress the noise made by escaping gas. This muffler is typically cylindrical in shape.

In operation, the pneumatic system of FIG. 2 is capable of providing a constant gas pressure output range in manifold 255 over a range of input gas pressures and gas usage. In general, pressurized gas enters pneumatic module 200 through manifold 235. The pressurized gas that enters pneumatic module 200 has been filtered and/or conditioned. The source of pressurized gas is typically a cylinder. Many physicians use cylinders of compressed nitrogen. In other cases, physicians may use another source of compressed air. Regardless of the source, compressed gas enters manifold 235 at any of a range of different pressures. For example, compressed gas in manifold 235 may be in a range of 60 psi to 120 psi (pounds per square inch). Depending on the source, compressed gas in manifold 235 may be at 60 psi, 120 psi, or any pressure in between.

Likewise, gas usage depends on the operation of the tools powered by the compressed gas contained in reservoir 215. Compressed gas passes through manifold 255, and typically through other components, to power various surgical tools. For example, compressed gas may be used to power a vitrector (not shown). The vitrector may consume different volumes of compressed gas depending on the manner in which it is operated. If the vitrector is operated at a slow cut rate, then it may consume a relatively small quantity of compressed gas over a period of time. If it is operated at a fast cut rate, then it may consume a relatively large quantity of compressed gas over a period of time. This range of gas usage may vary widely.

In general, the greater the gas usage from reservoir 215, the greater the amount of compressed gas must be input into reservoir 215 to maintain a constant gas pressure range. Likewise, the smaller the gas usage from reservoir 215, the smaller the amount of compressed gas must be input into reservoir 215 to maintain a constant gas pressure range. Accordingly, input proportional valve 205 is opened a certain percentage to allow a certain quantity of compressed gas to enter reservoir 215 for a given gas usage and input pressure. Likewise, output proportional valve 210 is opened a certain percentage to allow a certain quantity of compressed gas to exit reservoir 215 for a given gas usage and input pressure. As the gas usage and input pressure vary, the amount that proportional valves 205 and 210 are opened varies. Input and output proportional valves 205 and 210 are controlled independently to maintain a constant gas pressure range in reservoir 215 for a given gas usage and input pressure.

The constant gas pressure range maintained in reservoir 215 has a mid point that is typically a set point. A tight pressure range around this set point is maintained in reservoir 215. For example, depending on the gas pressure, the range may be plus or minus 0.5% or 0.05%.

Figure 3:
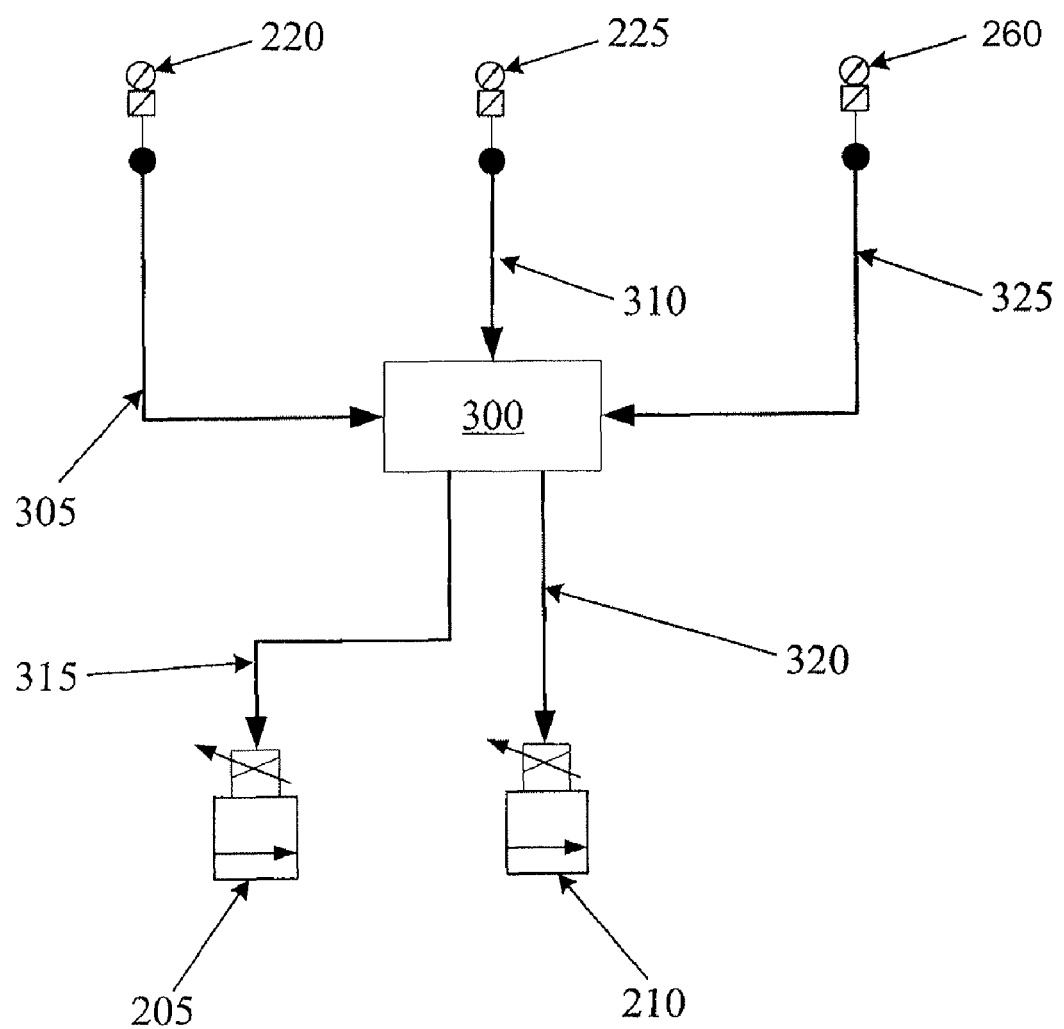
FIG. 3 is a schematic of a valve, transducer, and controller portion of a pneumatic system capable of providing a dynamic range of pressures according to an embodiment of the present invention.

FIG. 3 is a schematic of a valve, transducer, and controller portion of a pneumatic system capable of providing a dynamic range of pressures according to an embodiment of the present invention. In FIG. 3, controller 300 and interfaces 305, 310, 315, 320, and 325 are depicted along with proportional valves 205 and 210, and pressure transducers 220, 225, and 260.

In the embodiment of FIG. 3, controller 300 receives pressure information from pressure transducers 220, 225, and 260 via interfaces 305, 310, and 325, respectively. In this manner, pressure transducer 220 is electrically coupled to controller 300 via interface 305, pressure transducer 225 is electrically coupled to controller 300 via interface 310, and pressure transducer 260 is electrically coupled to controller 300 via interface 325. Controller 300 sends control signals to proportional valves 205 and 210 via interfaces 315 and 320, respectively.

Controller 300 is typically an intergraded circuit capable of performing logic functions. In this manner, controller 300 is in the form of a standard integrated circuit package with power, input, and output pins. In various embodiments, controller 300 is a valve controller or a targeted device controller. In such a case, controller 300 performs specific control functions targeted to a specific device, such as a valve. In other embodiments, controller 300 is a microprocessor. In such a case, controller 300 is programmable so that it can function to control valves as well as other components of the machine. In other cases, controller 300 is not a programmable microprocessor, but instead is a special purpose processor configured to control different valves that perform different functions.

Controller 300 is configured to receive signals from pressure transducers 220, 225, and 260 via interfaces 305, 310, and 325, respectively. These signals, for example, correspond to readings of gas pressure in manifolds 255 and 235. Controller 300 is also configured to send output signals via interfaces 315 and 320 to proportional valves 205 and 210, respectively. These output signals allow controller 300 to control the operation of proportional valves 205 and 210.

Interfaces 305, 310, and 325 are designed to carry signals from pressure transducers 220, 225, and 260 to controller 300. In this case, interfaces 305, 310, and 325 are common electrical conductors such as wires, buses, traces, or the like. Likewise, interfaces 315 and 320 carry signals from controller 300 to proportional valves 205 and 210. Interfaces 315 and 320 may be one or more wires, buses, traces, or the like designed to carry electrical or data signals.

In one embodiment consistent with the principles of the present invention, controller 300 implements a PID controller. A proportional-integral-derivative controller (PID controller) is a common feedback loop component in industrial control systems. A PID controller takes a measured value from a process or other apparatus and compares it with a reference set point value. The difference or error signal is then used to adjust some input to the process in order to bring the process' measured value back to its desired set point. Unlike simpler controllers, a PID controller can adjust process outputs based on the history and rate of change of the error signal, which gives more accurate and stable control.

In this embodiment, the set point is the pressure that is desired to be maintained in reservoir 215. This set point is effectively selected by the physician by depressing a foot-switch treadle. In one embodiment, the set point is selected by using a foot switch (not shown). Depressing the foot switch increases the pressure and the quantity of gas used during a given time period.

The input gas pressure and the gas usage also influence the operation of controller 300. For a given input pressure, as measured by input pressure transducer 260, proportional valves 205 and 210 are operated to maintain a constant pressure range in reservoir 215 over a range of gas usage. Proportional valves 205 and 210 are operated independently by controller 300. Controller 300 directs proportional valves 205 and 210 to open a certain percentage (e.g. 0%, 2%, 10%, 30%, 75%, 99%, 100%, etc.) to maintain a constant gas pressure range in reservoir 215.

In one embodiment consistent with the principles of the present invention, the input pressure of the pressurized gas in manifold 235 is measured by input pressure transducer 260. Based on this input pressure, a set of control constants is selected for use in a PID algorithm. Controller 300 uses this set of control constants to control the operation of proportional valves 205 and 210. Proportional valves 205 and 210 are adjusted by controller 300 to maintain a constant pressure range in reservoir 215 over a range of gas usage.

Figure 4:
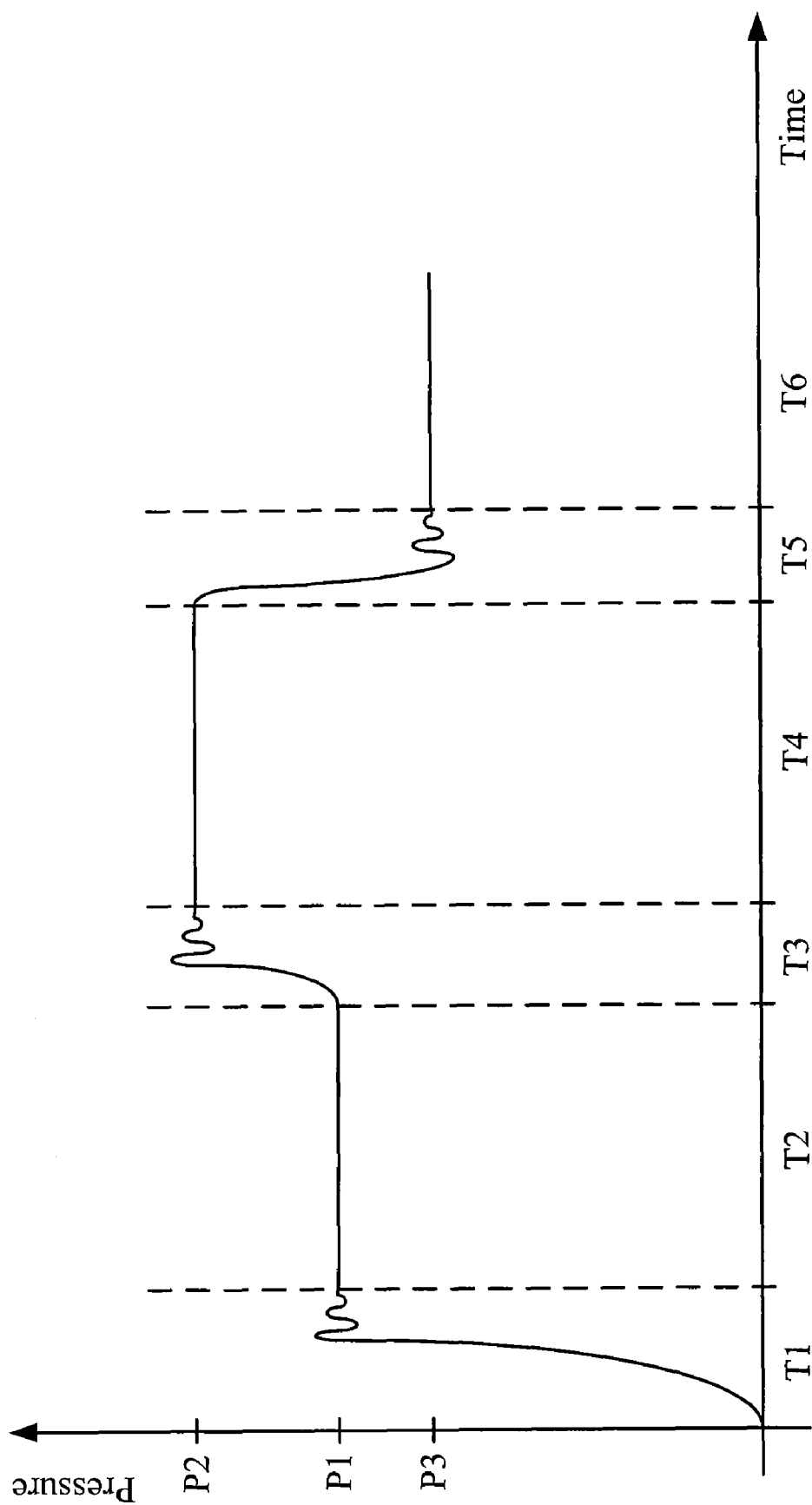
FIG. 4 is a graph depicting one method of operation of a pneumatic system capable of providing a dynamic range of pressures according to an embodiment of the present invention.

FIG. 4 is a graph depicting one method of operation of a pneumatic system capable of providing a dynamic range of pressures according to an embodiment of the present invention. In FIG. 4, the x-axis shows time, and the y-axis shows the pressure in reservoir 215. Three different gas pressures (P1, P2, and P3) are selected at three different times. The graph of FIG. 4 shows how the gas pressure in reservoir 215 responds to the control of proportional valves 205 and 210 by controller 300.

In time period T1, the gas pressure in reservoir 215 climbs from zero to P1. During this time period, proportional valves 205 and 210 are independently controlled by controller 300. For example, a surgeon may depress a foot switch to effectively select a set point of P1. In response to this selection, controller 300 operates proportional valves 205 and 210 to achieve a pressure of P1 in reservoir 215. As a result of the control algorithm selected, the pressure rises from zero, overshoots P1, and stabilizes at P1 after a very short period of time. Typically, the time period T1 is a very short period of time—on the order of milliseconds.

In time period T2, the gas pressure in reservoir 215 has settled out at the desired set point. In T2, the gas pressure in reservoir 215 is maintained in a tight gas pressure range around the selected set point.

In time period T3, the gas pressure in reservoir 215 climbs from P1 to P2. During this time period, proportional valves 205 and 210 are independently controlled by controller 300. For example, a surgeon may depress a foot switch to effectively select a set point of P2. In response to this selection, controller 300 operates proportional valves 205 and 210 to achieve a pressure range of P2 in reservoir 215. As a result of the control algorithm selected, the pressure rises from P1, overshoots P2, and stabilizes at P2 after a very short period of time. Typically, the time period T3 is a very short period of time—on the order of milliseconds.

In time period T4, the gas pressure in reservoir 215 has settled out at the desired set point. In T4, the gas pressure in reservoir 215 is maintained in a tight gas pressure range around the selected set point, in this case, P2.

In time period T5, the gas pressure in reservoir 215 goes from P2 to P3. During this time period, proportional valves 205 and 210 are independently controlled by controller 300. For example, a surgeon may activate a foot switch to effectively select a set point of P3. In response to this selection, controller 300 operates proportional valves 205 and 210 to achieve a pressure range of P3 in reservoir 215. As a result of the control algorithm selected, the pressure decreases from P2, undershoots P3, and stabilizes at P3 after a very short period of time. Typically, the time period T5 is a very short period of time—on the order of milliseconds.

In time period T6, the gas pressure in reservoir 215 has settled out at the desired set point. In T6, the gas pressure in reservoir 215 is maintained in a tight gas pressure range around the selected set point, in this case, P3.

From the above, it may be appreciated that the present invention provides an improved system for providing pneumatic power to a surgical tool. The present invention enables the provision of compressed gas over a variable range of pressures thus enabling the operation of a surgical tool over its complete functional range. Moreover, the pressure set point is dynamically adjustable, and the response time is short. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A pneumatic system for a surgical machine comprising:
   a reservoir for holding pressurized gas;
   a first proportional valve located on an input side of the reservoir, the first proportional valve configured to allow a first variable amount of pressurized gas to enter the reservoir;
   an input pressure transducer located on an input side of the first proportional valve, the input pressure transducer configured to measure a pressure of the pressurized gas entering the first proportional valve;
   a second proportional valve located on an output side of the reservoir, the second proportional valve configured to allow a second variable amount of pressurized gas to exit the reservoir;
   an output pressure transducer located on the output side of the reservoir, the output pressure transducer configured to measure a pressure of the gas exiting the reservoir; and
   a controller configured to control operation of the first and second proportional valves;
   wherein the controller is configured to receive a first signal from the input pressure transducer corresponding to the pressure of the pressurized gas entering the first proportional valve and a second signal from the output pressure transducer corresponding to the pressure of the pressurized gas exiting the reservoir, and wherein the controller is configured to use the first and second signals to adjust the first and second proportional valves to maintain a gas pressure in the reservoir within a range of gas pressures.

2. The system of claim 1, further comprising:
   a second, redundant output pressure transducer located on the output side of the reservoir, the second, redundant output pressure transducer configured to measure a pressure of the gas exiting the reservoir.

3. The system of claim 1 further comprising:
   a first manifold fluidly coupling an input pressure transducer to the first proportional valve;
   a second manifold fluidly coupling the first proportional valve to the reservoir;
   a third manifold fluidly coupling the reservoir to the second proportional valve;
   a fourth manifold fluidly coupling the second proportional valve to a venting port.

4. The pneumatic system of claim 1, wherein the second proportional valve is configured to allow the second variable amount of pressurized gas to exit the reservoir by venting through a venting port to the atmosphere.

5. The system of claim 1, wherein the controller is configured to adjust the first and second proportional valves so that a constant gas pressure range is maintained at an output of the reservoir over a first range of input gas pressures and a second range of gas usage.

6. The system of claim 5, wherein the constant gas pressure range that is maintained is selectable by actuation of a foot switch.

7. The system of claim 1, wherein the output side of the reservoir comprises a first path to provide pressurized air to the second proportional valve and a second path to provide pressurized air to the surgical machine, wherein at least a portion of the first path is separate from the second path.

8. The system of claim 1 wherein the controller is configured to maintain a gas pressure in the reservoir within a range of gas pressures that include a user selected gas pressure set point.

9. A pneumatic system for a surgical machine comprising:
a reservoir for holding pressurized gas;
a first proportional valve located on an input side of the reservoir, the first proportional valve configured to allow a variable amount of pressurized gas to enter the reservoir;
a second proportional valve located on an output side of a reservoir, the second proportional valve configured to allow a variable amount of pressurized gas to exit the reservoir;
a controller configured to control operation of the first and second proportional valves, thereby adjusting an amount of pressurized gas entering and exiting the reservoir;
a first interface electrically coupling the first proportional valve to the controller;
a second interface electrically coupling the second proportional valve to the controller;
an output pressure transducer located on the output side of the reservoir, the output pressure transducer configured to measure a pressure of the pressurized gas exiting the reservoir, the output pressure transducer electrically coupled to the controller; and
an input pressure transducer located on the input side of the reservoir, the input pressure transducer configured to measure a pressure of the pressurized gas near the first proportional valve, the input pressure transducer electrically coupled to the controller;
wherein the controller is configured to receive a first signal from the input pressure transducer corresponding to the pressure of the pressurized gas at the first proportional valve and a second signal from the output pressure transducer corresponding to the pressure of the pressurized gas exiting the reservoir, and wherein the controller is configured to implement a proportional integral derivative control algorithm using the first and second signals to adjust the first and second proportional valves to maintain a gas pressure in the reservoir within a range of gas pressures that include a user selected gas pressure set point.

10. The system of claim 9 further comprising:
a first manifold fluidly coupling the input pressure transducer to the first proportional valve;
a second manifold fluidly coupling the first proportional valve to the reservoir;
a third manifold fluidly coupling the reservoir to the second proportional valve; and
a fourth manifold fluidly coupling the second proportional valve to a venting port.

11. The pneumatic system of claim 9, wherein the second proportional valve is configured to allow the second variable amount of pressurized gas to exit the reservoir by venting through a venting port to the atmosphere.

12. The system of claim 9, wherein the controller is configured to use the first and second signals to adjust the first and second proportional valves so that a constant gas pressure range is maintained in the reservoir over a first range of input gas pressures and a second range of gas usage.

13. The system of claim 9, wherein the output side of the reservoir comprises a first path to provide pressurized air to the second proportional valve and a second path to provide pressurized air to the surgical machine, wherein at least a portion of the first path is separate from the second path.

14. The system of claim 13, wherein the constant gas pressure range that is maintained can be selected from a range of pressures.

15. The system of claim 9, wherein the user selected gas pressure set point is selectable by actuation of a foot switch.

* * * * *